United States Patent [19]

Eldin et al.

[11] Patent Number: 5,750,723

[45] Date of Patent: May 12, 1998

[54] POLYMERIZABLE DIKETOPYRROLOPYRROLES AND POLYMERS PREPARED THEREWITH

[75] Inventors: Sameer Hosam Eldin, Courtepin; Abul Iqbal, Arconciel; Zhimin Hao; Bernd Lamatsch, both of Marly, all of Switzerland

[73] Assignee: Ciba Specialty Chemicals Corporation, Tarrytown, N.Y.

[21] Appl. No.: 789,895

[22] Filed: Jan. 29, 1997

[30] Foreign Application Priority Data

Jan. 30, 1996 [CH] Switzerland ................. 228/96

[51] Int. Cl.$^6$ ..................... C07D 487/04
[52] U.S. Cl. ......................... 548/453
[58] Field of Search ....................... 548/453

[56] References Cited

U.S. PATENT DOCUMENTS

| | | | |
|---|---|---|---|
| 4,415,685 | 11/1983 | Iqbal et al. | 524/92 |
| 4,579,949 | 4/1986 | Rochat et al. | 546/167 |
| 4,778,899 | 10/1988 | Pfenninger et al. | 548/453 |
| 5,169,953 | 12/1992 | Mizuguchi et al. | 544/144 |
| 5,298,063 | 3/1994 | Mizuguchi et al. | 106/21 D |
| 5,484,943 | 1/1996 | Zambonnis et al. | 548/453 |
| 5,591,865 | 1/1997 | Hao et al. | 548/453 |
| 5,616,725 | 4/1997 | Zambonnis et al. | 548/453 |

FOREIGN PATENT DOCUMENTS

| | | |
|---|---|---|
| 0337951 | 10/1989 | European Pat. Off. . |
| 0563901 | 10/1993 | European Pat. Off. . |
| 0648770 | 4/1995 | European Pat. Off. . |
| 0656403 | 6/1995 | European Pat. Off. . |
| 0704497 | 4/1996 | European Pat. Off. . |

*Primary Examiner*—Joseph McKane
*Attorney, Agent, or Firm*—Kevin T. Mansfield

[57] ABSTRACT

1,4-diketopyrrolopyrroles of the formula

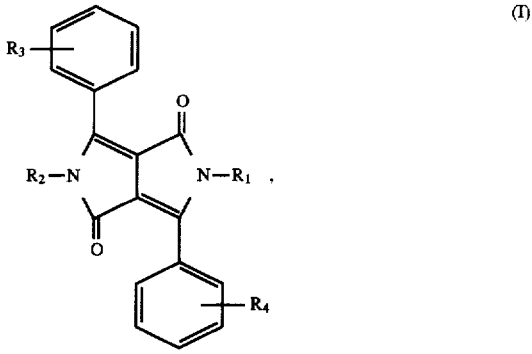

(I)

in which $R_1$ and $R_2$ independently of one another are hydrogen, $C_{12}-C_{24}$alkyl, $C_6-C_{24}$alkyl which is interrupted one or more times by O or S, or are a group of the formula

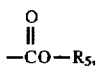

in which $R_5$ is $C_4-C_{18}$alkyl or $C_5-C_{10}$cycloalkyl, $R_3$ is a polymerizable reactive group, $R_4$, if $R_1$ and $R_2$ are hydrogen, is $C_6-C_{24}$alkyl which is attached directly or by way of O or S to the benzene ring and is uninterrupted or is interrupted one or more times by O or S, and $R_4$, if $R_1$ and/or $R_2$ are $C_{12}-C_{24}$alkyl, is $C_6-C_{24}$alkyl which is interrupted one or more times by O or S or is a group

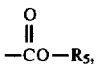

hydrogen, halogen, methyl, methoxy, CN or phenyl, or is the same as $R_3$.

7 Claims, No Drawings

POLYMERIZABLE DIKETOPYRROLOPYRROLES AND POLYMERS PREPARED THEREWITH

The present invention relates to novel diketopyrrolopyrroles containing polymerizable reactive groups, and to polymers prepared therewith.

The diketopyrrolopyrrole pigments which are now referred to in the literature as well, for example in the Colour Index, as DPP pigments, and which have been known for some years and found to be useful, are described inter alia in U.S. Pat. No. 4,415,685 and U.S. Pat. No. 4,579,949.

EP-A 337951 describes colour polymer microparticles which can be obtained by polymerizing pigment derivatives which contain polymerizable reactive groups into various kinds of polymers. Mention is made in this context of derivatives of a wide variety of classes of pigment, including DPP derivatives, and specifically one member thereof, a 1,4-diketo-3,6-diphenylpyrrolo[3,4-c]pyrrole substituted on both nitrogen atoms by an ethyl methacrylate group.

However, it has been found that the copolymerization of this compound does not take place satisfactorily.

It has now been found that it is nevertheless possible, by introducing specific, long-chain reactive groups, to obtain DPP chromophores which, surprisingly, can be reacted readily with polymers or to form polymers, whether directly, by homo- or copolymerization, or else by grafting onto existing, preformed homo- or copolymers.

The present invention accordingly provides 1,4-diketopyrrolopyrroles of the formula

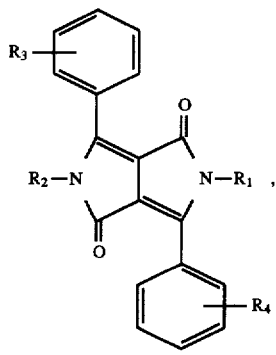
(I)

in which $R_1$ and $R_2$ independently of one another are hydrogen, $C_{12}-C_{24}$alkyl, $C_6-C_{24}$alkyl which is interrupted one or more times by O or S, or are a group of the formula

$-CO-R_5$, in which $R_5$ is $C_4-C_{18}$alkyl, or $C_5-C_{10}$cycloalkyl, $R_3$ is a polymerizable reactive group, $R_4$, if $R_1$ and $R_2$ are hydrogen, is $C_6-C_{24}$alkyl which is attached directly or by way of O or S to the benzene ring and is uninterrupted or is interrupted one or more times by O or S, and $R_4$, if $R_1$ and/or $R_2$ are $C_{12}-C_{24}$alkyl, is $C_6-C_{24}$alkyl which is interrupted one or more times by O or S or is a group,

$-CO-R_5$, hydrogen, halogen, methyl, methoxy, CN or phenyl, or is the same as $R_3$.

The term polymerizable reactive groups refers, for example, to groups capable of addition polymerization, for example acrylate radicals, or groups capable of condensation polymerization, for example hydroxyl or acid chloride groups, or else groups capable of polyaddition, for example hydroxyl or isocyanate groups.

Preferably $R_3$ is OH, SH, $NH_2$, CHO, NCO, hydroxyphenyl, $-CH=CH_2$, $-CH=CH-COOR_6$, $-CH=CH-CN$, $-O-C(O)-CH=CH_2$, $-O-C(O)-C(Me)=CH_2$,

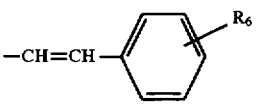

or $COOR_6$, in which $R_6$ is hydrogen or $C_1-C_6$alkyl, or $R_3$ is a radical of the formula

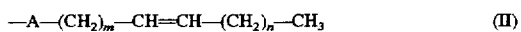
(II)

or

(III)

in which A is $-O-$, $-NH-$ or $-COO-$, m and n independently of one another are an integer between zero and 12, and p and r, independently of one another, are zero or 1, X is methylene or $C_2-C_{18}$alkylene which is uninterrupted or is interrupted one or more times by $-O-$ and/or $-S-$, $-NH-$, phenylene, $-COO-$, $-CONH-$, or

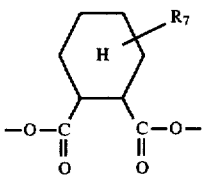

in which $R_7$ is hydrogen or methyl,

Y is

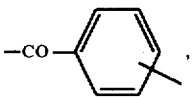

$-Si(Cl)_2-$, $-Si(OC_2H_5)_2-$, $-Si(OCOCH_3)_2-$, $CH_2-CH(OH)-$ or $-CH(CN)-$ and Z is $-O-$, $-NH-$, $-COO-$, phenylene,

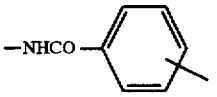

$-Si(Cl)_2-$, $-Si(OC_2H_5)_2-$ or $-Si(OCOCH_3)_2-$,

Q is $-OH$, $-NH_2$, glycidyl, $-CHO$, $-NCO$, $-CH=CH_2$, $-C(CH_3)=CH_2$, $-CO-CH=CH_2$, $-CO-C(CH_3)=CH_2$, $C_5-C_7$cycloalkenyl,

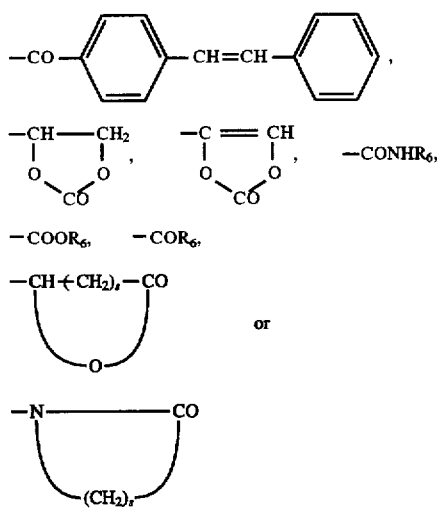

where s is an integer from 1 to 6.

Any halogen substituents are, for example, iodine, fluorine, chlorine or bromine, preferably bromine or chlorine, particularly preferably chlorine;

$C_1$–$C_4$alkyl is methyl, ethyl, n-propyl, isopropyl, n-butyl, isobutyl, sec-butyl or tert-butyl;

$C_1$–$C_6$alkyl is, for example, methyl, ethyl, n-propyl, isopropyl, n-butyl, isobutyl, sec-butyl, tert- butyl, n-amyl, tert-amyl or hexyl;

$C_4$–$C_{24}$alkyl is, for example, n-butyl, isobutyl, sec-butyl, tert-butyl, n-amyl, tert-amyl, hexyl, heptyl, octyl, 2-ethylhexyl, nonyl, decyl, dodecyl, tetradecyl, hexadecyl, octadecyl, eicosyl, heneicosyl, docosyl or tetracosyl;

$C_6$–$C_{18}$alkyl is, for example, hexyl, heptyl, octyl, 2-ethylhexyl, nonyl, decyl, dodecyl, tetradecyl, hexadecyl or octadecyl;

$C_6$–$C_{24}$alkyl is, for example, hexyl, heptyl, octyl, 2-ethylhexyl, nonyl, decyl, dodecyl, tetradecyl, hexadecyl, octadecyl, eicosyl, heneicosyl, docosyl or tetracosyl; and $C_{12}$–$C_{18}$alkyl is, for example, dodecyl, tetradecyl, hexadecyl or octadecyl;

$R_5$ as $C_4$–$C_{18}$alkyl is straight-chain alkyl or, especially in the case of relatively short chains, is branched alkyl, for example, tert-butyl, n-pentyl, tert-amyl, n-hexyl, 2,2-dimethylbutyl, n-octyl, 1,1,3,3-tetramethylbutyl, 2-ethylhexyl, nonyl, decyl, dodecyl, tetradecyl, hexadecyl or octadecyl.

$C_5$–$C_{10}$cycloalkyl is, for example, cyclopentyl, cyclohexyl, cycloheptyl, trimethylcyclohexyl, especially cyclohexyl.

$C_5$–$C_7$ cycloalkenyl is, for example, mono- or bicyclic cycloalkenyl, for example, cyclopentenyl, cyclohexenyl or norbornenyl.

Some examples of the radical —$(Y)_p$—X—$(Z)_r$—Q in formula III are

—$(CH_2)_6$—OH, —$(CH_2)_{10}$—OH, —$(CH_2)_{11}$—OH, —$(CH_2)_6$—OCO—CH=$CH_2$, —$(CH_2)_6$—OCO—C($CH_3$)=$CH_2$,

—$(CH_2)_{10}$—OCO—CH=$CH_2$, —$(CH_2)_{10}$—OCO—C($CH_3$)=$CH_2$, —$(CH_2)_{11}$—OCO—CH=$CH_2$, —$(CH_2)_{11}$—OCO—C($CH_3$)=$CH_2$,

—$(CH_2)_2$—O—$(CH_2)_2$—O—$(CH_2)_2$—OH

—$(CH_2)_2$—O—$(CH_2)_2$—O—$(CH_2)_2$—O—CO—CH=$CH_2$

—$(CH_2)_2$—O—$(CH_2)_2$—O—$(CH_2)_2$—O—CO—C($CH_3$)=$CH_2$

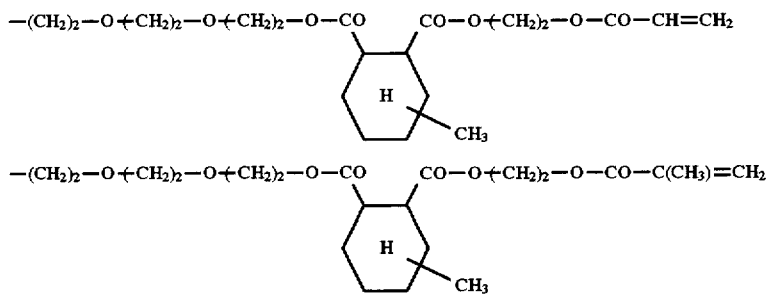

—$(CH_2)_3$—S—$(CH_2)_2$—OH
—$(CH_2)_3$—S—$(CH_2)_6$—OH
—$(CH_2)_3$—S—$(CH_2)_2$—COOH
—$(CH_2)_3$—S—$(CH_2)_6$—COOH
—$(CH_2)_3$—S—$(CH_2)_2$—$NH_2$
—$(CH_2)_3$—S—$(CH_2)_6$—$NH_2$
—$(CH_2)_3$—S—$(CH_2)_2$—O—$(CH_2)_2$—O—$(CH_2)_2$—OH
—$(CH_2)_3$—S—$(CH_2)_2$—O—$(CH_2)_2$—O—$(CH_2)_2$—$NH_2$

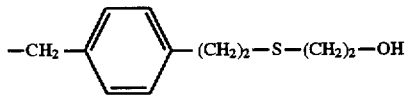

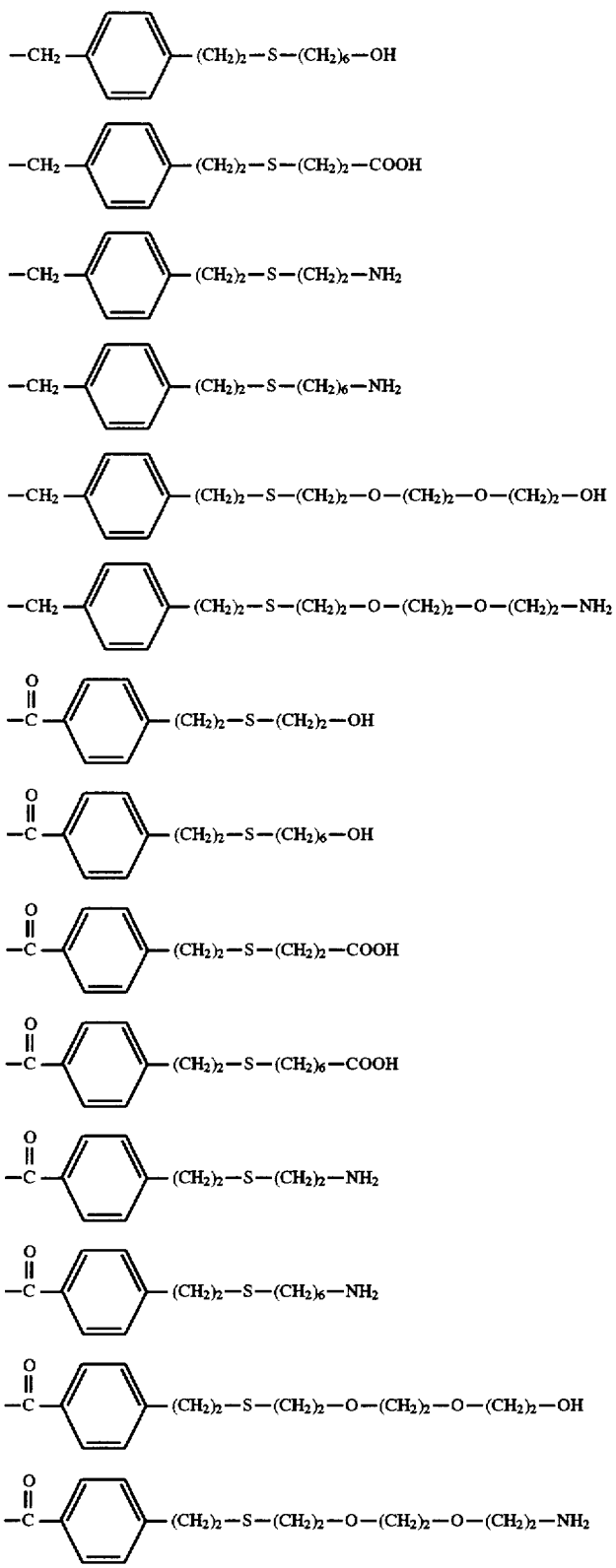
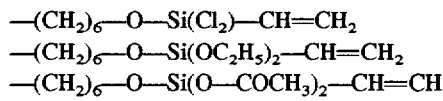
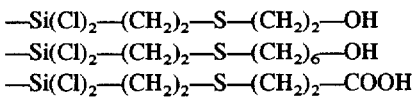

—Si(Cl)$_2$—(CH$_2$)$_2$—S—(CH$_2$)$_2$—NH$_2$
—Si(Cl)$_2$—(CH$_2$)$_2$—S—(CH$_2$)$_6$—NH$_2$
—Si(Cl)$_2$—(CH$_2$)$_2$—S—(CH$_2$CH$_2$O)$_2$—CH$_2$CH$_2$OH
—Si(Cl)$_2$—(CH$_2$)$_2$—S—(CH$_2$CH$_2$O)$_2$—CH$_2$CH$_2$NH$_2$
—Si(OC$_2$H$_5$)$_2$—(CH$_2$)$_2$—S—(CH$_2$)$_2$—OH
—Si(OC$_2$H$_5$)$_2$—(CH$_2$)$_2$—S—(CH$_2$)$_6$—OH
—Si(OC$_2$H$_5$)$_2$—(CH$_2$)$_2$—S—(CH$_2$)$_2$—COOH
—Si(OC$_2$H$_5$)$_2$—(CH$_2$)$_2$—S—(CH$_2$)$_6$—COOH
—Si(OC$_2$H$_5$)$_2$—(CH$_2$)$_2$—S—(CH$_2$)$_2$—NH$_2$
—Si(OC$_2$H$_5$)$_2$—(CH$_2$)$_2$—S—(CH$_2$)$_6$—NH$_2$
—Si(OC$_2$H$_5$)$_2$—(CH$_2$)$_2$—S—(CH$_2$CH$_2$O)$_2$—CH$_2$CH$_2$OH
—Si(OC$_2$H$_5$)$_2$—(CH$_2$)$_2$—S—(CH$_2$CH$_2$O)$_2$—CH$_2$CH$_2$NH$_2$
—Si(OCOCH$_3$)$_2$—(CH$_2$)$_2$—S—(CH$_2$)$_2$—OH
—Si(OCOCH$_3$)$_2$—(CH$_2$)$_2$—S—(CH$_2$)$_6$—OH
—Si(OCOCH$_3$)$_2$—(CH$_2$)$_2$—S—(CH$_2$)$_2$—COOH
—Si(OCOCH$_3$)$_2$—(CH$_2$)$_2$—S—(CH$_2$)$_6$—COOH
—Si(OCOCH$_3$)$_2$—(CH$_2$)$_2$—S—(CH$_2$)$_2$—NH$_2$
—Si(OCOCH$_3$)$_2$—(CH$_2$)$_2$—S—(CH$_2$)$_6$—NH$_2$
—Si(OCOCH$_3$)$_2$—(CH$_2$)$_2$—S—(CH$_2$CH$_2$O)$_2$—CH$_2$CH$_2$OH
—Si(OCOCH$_3$)$_2$—(CH$_2$)$_2$—S—(CH$_2$CH$_2$O)$_2$—CH$_2$CH$_2$NH$_2$
—CH$_2$CH(OH)—CH$_2$—S—(CH$_2$)$_6$—COOH
—CH$_2$CH(OH)—CH$_2$—S—(CH$_2$)$_6$—OH
—CH$_2$CH(OH)—CH$_2$—S—(CH$_2$CH$_2$O)$_2$—CH$_2$CH$_2$OH
—CH$_2$CH(OH)—CH$_2$—S—(CH$_2$CH$_2$O)$_2$—CH$_2$CH$_2$COOH
—CH$_2$CH(OH)—CH$_2$—NH—(CH$_2$)$_6$—COOH
—CH$_2$CH(OH)—CH$_2$—NH—(CH$_2$)$_6$—OH
—CH$_2$CH(OH)—CH$_2$—NH—(CH$_2$CH$_2$O)$_2$—CH$_2$CH$_2$OH
—CH$_2$—CONH—(CH$_2$)$_6$—OH
—CH$_2$—CONH—(CH$_2$)$_6$—COOH
—CH$_2$—CONH—(CH$_2$CH$_2$O)$_2$—CH$_2$CH$_2$OH

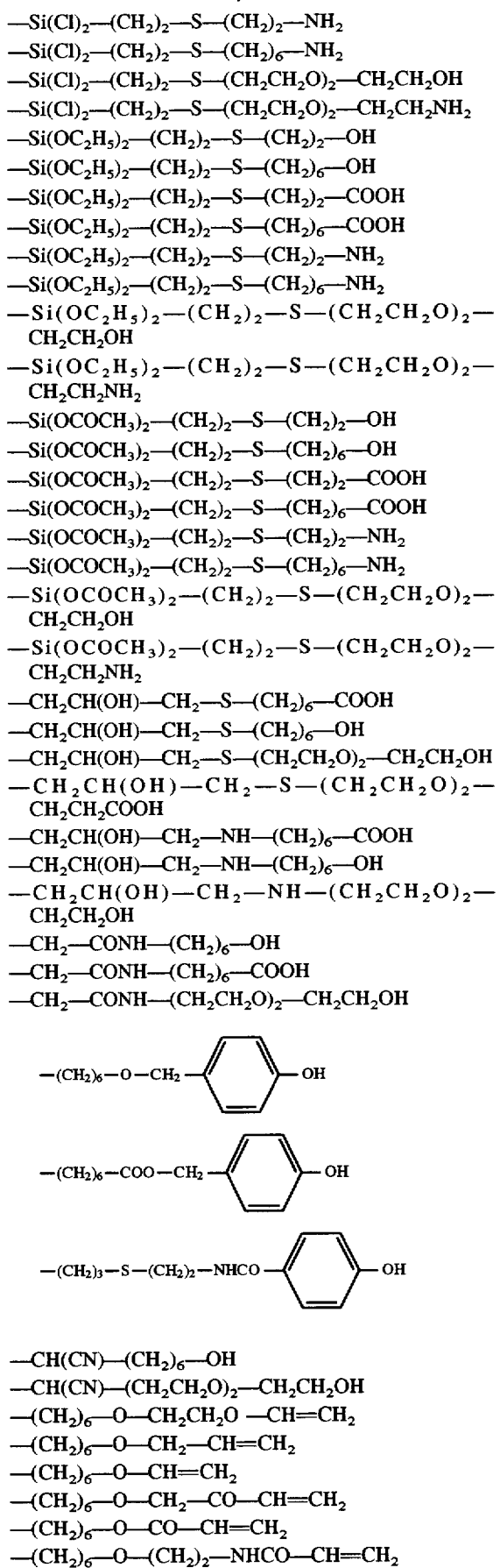

—CH(CN)—(CH$_2$)$_6$—OH
—CH(CN)—(CH$_2$CH$_2$O)$_2$—CH$_2$CH$_2$OH
—(CH$_2$)$_6$—O—CH$_2$CH$_2$O—CH=CH$_2$
—(CH$_2$)$_6$—O—CH$_2$—CH=CH$_2$
—(CH$_2$)$_6$—O—CH=CH$_2$
—(CH$_2$)$_6$—O—CH$_2$—CO—CH=CH$_2$
—(CH$_2$)$_6$—O—CO—CH=CH$_2$
—(CH$_2$)$_6$—O—(CH$_2$)$_2$—NHCO—CH=CH$_2$

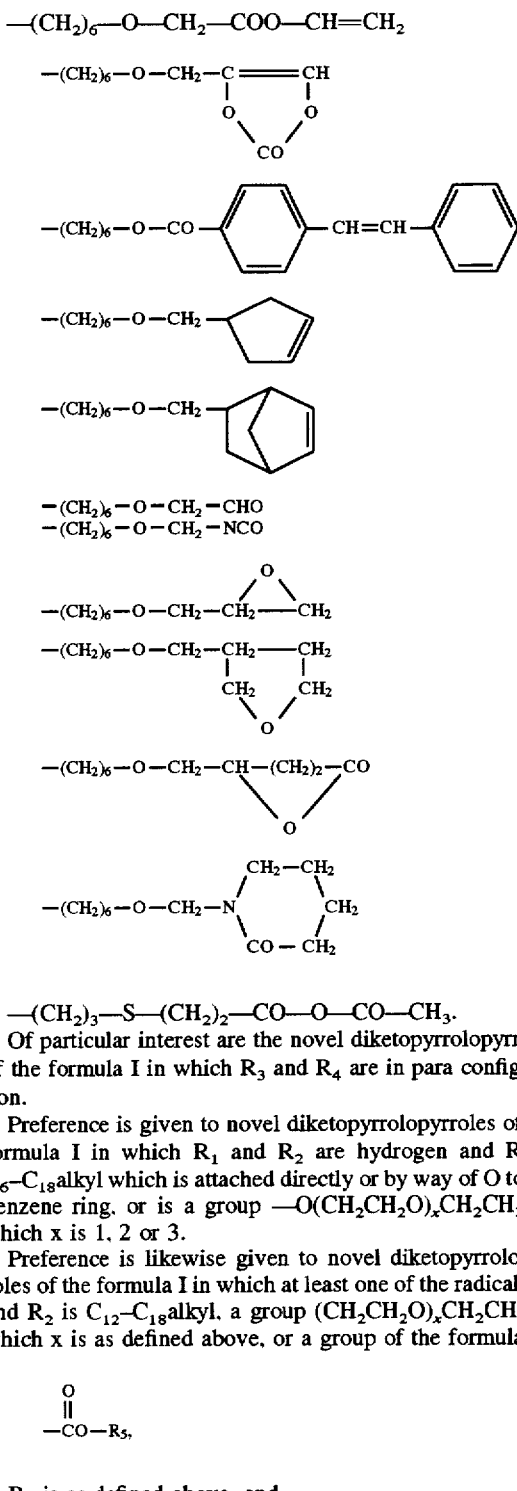

—(CH$_2$)$_3$—S—(CH$_2$)$_2$—CO—O—CO—CH$_3$.

Of particular interest are the novel diketopyrrolopyrroles of the formula I in which R$_3$ and R$_4$ are in para configuration.

Preference is given to novel diketopyrrolopyrroles of the formula I in which R$_1$ and R$_2$ are hydrogen and R$_4$ is C$_6$–C$_{18}$alkyl which is attached directly or by way of O to the benzene ring, or is a group —O(CH$_2$CH$_2$O)$_x$CH$_2$CH$_3$, in which x is 1, 2 or 3.

Preference is likewise given to novel diketopyrrolopyrroles of the formula I in which at least one of the radicals R$_1$ and R$_2$ is C$_{12}$–C$_{18}$alkyl, a group (CH$_2$CH$_2$O)$_x$CH$_2$CH$_3$, in which x is as defined above, or a group of the formula $$-\overset{\overset{O}{\|}}{C}-R_5,$$

R$_3$ is as defined above, and

R$_4$ is hydrogen or is as defined for R$_3$.

With particular preference, R$_3$ is OH, NH$_2$ or a radical of the formula

—X—(O)$_r$—Q          (IV)

in which

X is C$_4$–C$_{12}$alkylene which is uninterrupted or is interrupted 1, 2 or 3 times by O and/or once by —S—, —NH—or

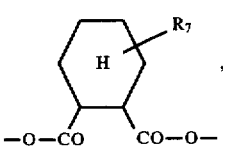

r and $R_7$ are as defined above, and

Q is —OH; —CH=$CH_2$, —C($CH_3$)=$CH_2$, —CO—CH=$CH_2$ or —CO—C($CH_3$)=$CH_2$.

X is preferably —($CH_2$)$_q$—, where q can be an integer between 6 and 12, such as 6, 7,8,9,10,11 or 12, or X is —($CH_2CH_2O$)$_2$—$CH_2CH_2$—or

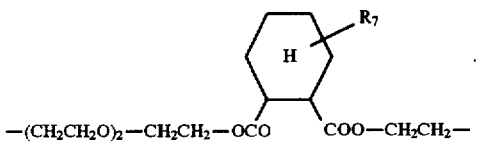

The novel diketopyrrolopyrroles are preferably prepared by reacting a succinic diester with a nitrile, which involves reacting (step a) an asymmetric or symmetric dialkyl or diaryl succinate, or a monoalkyl monoaryl succinate or dicyclohexyl succinate, with a nitrile of the Formula

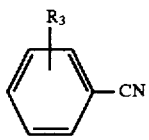

or with a mixture, preferably an equimolar mixture, of the nitriles of the formulae

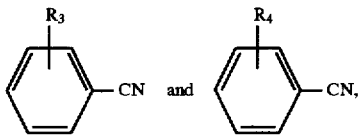

where $R_3$ and $R_4$ are as defined above and may additionally be customary protective groups for, for example, the —OH group, or for generating a —CHO group, such as $C_1$–$C_4$alkoxy, especially methoxy, preferably in para position, and the 1,3-dioxan-2-yl group, preferably in para position, in the desired molar ratio in an organic solvent in the presence of a strong base such as an alkali metal, especially sodium, an alkali metal amide, such as sodium amide, an alkali metal hydride, such as sodium hydride, or an alkali metal alcoholate, especially with a $C_1$–$C_5$alkanol, such as NaOMe, NaO-tert-amyl, and then hydrolysing the reaction product and, if desired, isolating the desired product.

If desired it is possible in a step (b) to react the resulting diketopyrrolopyrroles of the formula 1 in which $R_1$ and $R_2$ are hydrogen with (b1) a dicarbonate of the formula XI,

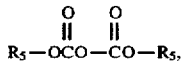

in the desired molar ratio, or (b2) in the desired molar ratio with a halogen compound of the formula XII, $R_1$—Hal, in which $R_1$ is $C_{12}$–$C_{24}$alkyl or is $C_6$–$C_{24}$alkyl interrupted one or more times by O or S, or (b3) in the desired molar ratio with a halogen compound such as Hal—($CH_2$)$_m$—CH=CH—($CH_2$)$_n$—$CH_3$, or Hal—(Y)$_p$—X—(Z)$_r$—Q, in which m, n, p, r, Y, X, Q and Z are as defined above and Hal is fluorine, chlorine, bromine or iodine, especially chlorine or bromine.

It is furthermore possible, in a third step (c) directly prior to or following step (b), if desired to react diketopyrrolopyrroles of the formula I in which $R_3$ and/or $R_4$ are protective groups, preferably the methoxy group or the 1,3-dioxan-2-yl group, in a customary manner, for example by hydrolysis, to give the corresponding desired target molecule. Thus it is possible, for example, to transform the methoxy group into the —OH group and the 1,3-dioxan-2-yl group into a —CHO group by known methods.

The choice of the reaction parameters can be made, for example, in analogy to the method described in U.S. Pat. No. 4,579,949; consequently, further details of this are unnecessary.

Furthermore, in a preferred embodiment, the novel diketopyrrolopyrroles of the formula I in which $R_1$ and $R_2$ are hydrogen can prepared, for example, by reacting a pyrrolinone of the formula

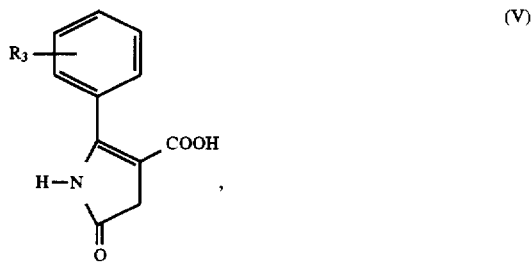

(V)

in which R is, for example, $C_1$–$C_4$alkyl, with a nitrile of the formula

(VI)

where $R_3$ and $R_4$ are as defined above, in analogy to the method described in U.S. Pat. No. 4,778,899.

Pyrrolinones of the formula V are customarily obtained by methods known per se, for example by cyclizing a compound of the formula

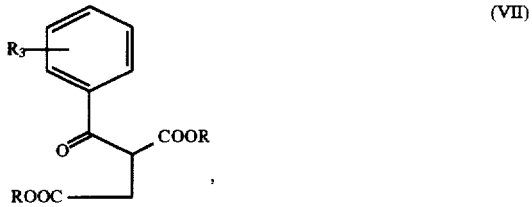

(VII)

in which $R_3$ and R are as defined above, with an ammonium salt, as decribed for example in U.S. Pat. No. 4,778,899.

The compounds of the formula VII and the nitriles of the formula VI are known and/or can be prepared by methods known per se.

Nitriles of the formula VI in which $R_4$ is $C_4$–$C_{24}$alkyl which is attached by way of O or S and which is uninterrupted or is interrupted by O or S can be obtained, for example, from hydroxybenzonitrile, by reaction with a halogen compound of the formula $R_4$—Hal in accordance with known methods. Compounds of the formula VII in which $R_3$ is a group —A—(CH$_2$)$_m$—CH=CH—(CH$_2$)$_n$—CH$_3$ (II) or —A—(Y)$_p$—X—(Z)$_r$—Q (III)

can be obtained analogously by reacting a diester of the formula

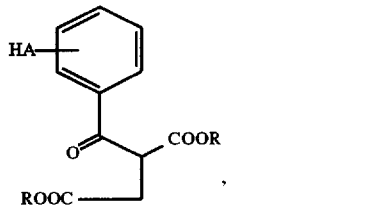
(VIII)

in which A and R are as defined above, with a halogen compound of the formula

Hal—(CH$_2$)$_m$—CH=CH—(CH$_2$)$_n$—CH$_3$ (IX) or

Hal—(Y)$_p$—X—(Z)$_r$—Q (X)

where the compounds of the formulae VIII, IX and X are substances which are known or are in any case readily available to the skilled worker. Hal is halogen such as fluorine, chlorine, bromine or iodine, preferably chlorine or bromine, particularly preferably chlorine.

Novel diketopyrrolopyrroles of the formula I in which $R_1$ and $R_2$ are hydrogen and $R_3$ and possibly also $R_4$ are —CH=CH—COOR$_6$, —CH=CH—CN or

can, in a further preferred embodiment, likewise be prepared by known methods, for example in accordance with R. F. Heck, Organic Reactions, 27 (1982) 345 from diketopyrrolopyrroles of the formula I in which $R_1$ and $R_2$ are hydrogen and $R_3$ and/or $R_4$ are halogen.

Novel diketopyrrolopyrroles of the formula I in which $R_1$ and/or $R_2$ are a group

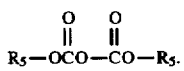

can be obtained, for example, in a further preferred embodiment, by methods known per se such as are described, for example, in EP-A 0648770 by reacting corresponding diketopyrrolopyrroles of the formula I in which $R_1$ and $R_2$ are hydrogen in the desired molar ratio with a dicarbonate of the formula $$R_5—OCO—CO—R_5.$$ (XI)

Dicarbonates for the formula XI are known and/or are compounds accessible by known methods.

Novel diketopyrrolopyrroles of the formula I in which $R_1$ and/or $R_2$ are $C_{12}$–$C_{24}$alkyl or are $C_6$–$C_{24}$alkyl which is interrupted one or more times by O or S can, in a further preferred embodiment, be obtained by methods known per se, by reacting corresponding diketopyrrolopyrroles of the formula I in which $R_1$ and $R_2$ are hydrogen in the desired molar ratio with a halogen compound of the formula $R_1$—Hal (XII)

in which $R_1$ is $C_{12}$–$C_{24}$alkyl or is $C_6$–$C_{24}$alkyl which is interrupted one or more times by O or S.

Using, for example, 1 mol equivalent of the compound of the formula XI or XII, a DPP is normally obtained of the formula I, in which $R_2$ is hydrogen; if 2 mole equivalents, for example, are used, then a DPP derivative is generally obtained in which the particles $R_1$ and $R_2$ are identical.

If $R_3$ in novel diketopyrrolopyrroles of this type is a group of the formula II or III, then this group can be introduced by reaction with halogen compounds of the formulae IX and/or X, in accordance with the method described above in connection with the preparation of the compounds of the formula VII, prior to or preferably after the reaction with the dicarbonate.

Similarly, by reacting diketopyrrolopyrroles of the formula I in which $R_1$ and $R_2$ are hydrogen in the desired molar ratio with halogen compounds of the formulae IX and X, it is also possible to prepare diketopyrrolopyrroles of the formula

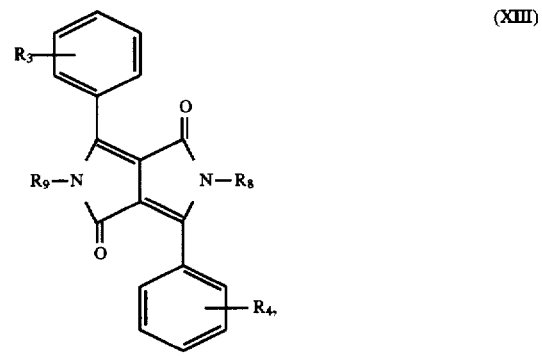
(XIII)

in which $R_8$ is a group

—(CH$_2$)$_m$—CH=CH—(CH$_2$)$_n$—CH$_3$ or

—(Y)$_p$—X—(Z)$_r$—Q and $R_9$ is hydrogen or is $R_8$, and $R_3$, $R_4$, X, Y, Z, Q, m, n, p and r are as defined above.

The diketopyrrolopyrroles of the formula XIII, which are particularly suitable for preparing multiply crosslinked polymers, form a further subject of the present application.

The novel DPP compounds can be used very readily, by virtue of their reactive groups, for preparing or modifying polymers. The coloured polymers modified or prepared in this way unexpectedly exhibit advantageous colour effects and—depending on the amount of DPP compound used—a wide variety of shades, which may differ entirely from those of the corresponding DPP pigments which possess no polymerizable groups.

The present invention provides, furthermore, a method of preparing or modifying polymers by a polymerization reaction or polymer-analogous reaction, which involves polymerizing a diketopyrrolopyrrole of the forumula I, in the presence if desired of a customary comonomer, for example one carrying at least one carbon-carbon double bond, or of a polymer which carries polymerizable groups.

In a preferred embodiment of this invention coloured (co)polymers can be prepared by polyreacting a mixture of the novel DPP momoners and further customary and suitable monomers in a liquid phase, e.g. in a melt, solution, suspension or emulsion.

These novel DPP polymers are commonly prepared in accordance with generally known methods, for example either by a polymerization reaction, i.e. by addition polymerization (thermal or photochemical), condensation polymerization or polyaddition, or by a polymeranalogous reaction, i.e. by reacting the novel DPP compounds, containing suitable reactive groups, with existing polymers which themselves have reactive groups (grafting).

In accordance with observations made to date, the novel DPP compounds (DPP monomers) can be used to conduct all known types of polymerization reaction. Thus it is possible, for example, to use DPP monomers whose reactive groups have C=C bonds to prepare vinyl, allyl, vinyl ester, vinyl amide, vinyl acetate or vinyl ketone polymers; to use monofunctional DPP monomers whose reactive groups contain heteroatoms to prepare polyaldehydes, polyisocyanates, polyepoxides, polyethers, polyacetones or polylactams; to use bifunctional DPP monomers whose reactive groups contain heteroatoms to prepare polyesters, polyamides, polyimides or polycarbonates by way of condensation polymerization, and polyepoxides, polyurethanes or polyimides by way of polyaddition, it being possible for the polymerization to involve free-radical, cationic or anionic polymerization, coordination polymerization or group-transfer polymerization.

Examples of the preparation of DPP polymers, starting from the novel DPP monomers, include: Addition polymerization: DPP polyacrylates by free-radical thermal polymerization of DPP acrylates; DPP polyacrylates by free-radical photopolymerization of DPP acrylates.

Condensation polymerization: DPP polyesters from DPP diols and di-acid chlorides; DPP polycarbonates from DPP diols and phosgene.

Polyaddition: DPP polyurethanes from DPP diols and diisocyanates; DPP polyepoxides from DPP epoxides and amines.

Polymer-analogous reaction: Reaction of a DPP alcohol with a polymer which has been prepared from styrene and maleic anhydride, and thus contains anhydride groups, to form a polymer containing DPP mono- or diester groups.

The novel DPP polymers may also include additives, such as light stabilizers, antioxidants and UV absorbers, which can be added during or after actual polymerization, also for example during the processing of the polymers (extrusion). These additives may themselves also have polymerizable reactive groups, and in this case can be copolymerized together with the DPP monomers.

The DPP polymers prepared in accordance with this invention and which hereinafter will be understood as including also copolymers prepared from novel DPP polymers and other customary monomers, are advantageously suited to many purposes, such as for colouring high molecular weight organic materials, e.g. biopolymers, plastic materials, including fibres, glasses, ceramic products, for formulations in decorative cosmetics, for the preparation of inks, printing inks, paint systems, in particular automotive lacquers and photoresists, photo- and electroconductive polymers, fluorescent whitening agents, photocell aggregates, coloured photoresists and dispersion colours and, furthermore, the novel diketopyrrolopyrroles can be used in the biomedical field of application, e.g. for the preparation of diagnostic agents as well as in the fields of impact-printing and non-impact-printing and photo/repro in general.

Illustrative examples of suitable organic materials of high molecular weight which can be coloured with the DPP polymers of this invention are vinyl polymers, for example polystyrene, poly-α-methylstyrene, poly-p-methylstyrene, poly-p-hydroxystyrene, poly-p-hydroxy-phenylstyrene, polymethyl methacrylate and polyacrylamide as well as the corresponding methacrylic compounds, polymethylmaleate, polyacrylonitrile, polymethacrylonitrile, polyvinyl chloride, polyvinyl fluoride, polyvinylidene chloride, polyvinylidene fluoride, polyvinyl acetate, polymethyl vinyl ether and polybutyl vinyl ether; polymers which are derived from malein-imide and/or maleic anhydride, such as copolymers of maleic anhydride with styrene; polyvinyl pyrrolidone; ABS; ASA; polyamides; polyimides; polyamidimides; polysulfones; polyether sulfones; polyphenylene oxides; polyurethanes; polyureas; polycarbonates; polyarylenes; polyarylene sulfides; polyepoxides; polyolefins such as polyethylene and polypropylene; polyalkadienes; biopolymers and the derivatives thereof e.g. cellulose, cellulose ethers and esters such as ethylcellulose, nitrocellulose, cellulose acetate and cellulose butyrate, starch, chitin, chitosan, gelatine, zein; natural resins; synthetic resins such as alkyd resins, acrylic resins, phenolic resins, epoxide resins, aminoformaldehyde resins such as urea/formaldehyde resins and melamine/formaldehyde resin; vulcanized rubber; casein; silicone and silicone resins; rubber, chlorinated rubber; and also polymers which are used, for example, as binders in paint systems, such as novolaks which are derived from $C_1$–$C_6$-aldehydes such as formaldehyde and acetaldehyde and a binucluear or mononuclear, preferably mononuclear, phenol which, if desired, is substituted by one or two $C_1$–$C_9$alkyl groups, one or two halogen atoms or one phenyl ring, such as o-, m- or p-cresol, xylene, p-tert-butylphenol, o-, m- or p-nonylphenol, p-chlorophenol or p-phenylphenol, or a compound having more than one phenolic group such as resorcinol, bis(4-hydroxyphenyl)-methane or 2,2-bis(4-hydroxyphenyl)propane; as well as suitable mixtures of said materials.

Particularly preferred high molecular weight organic materials, in particular for the preparation of a paint system, a printing ink or ink, are, for example, cellulose ethers and esters, e.g. ethylcellulose, nitrocellulose, cellulose acetate and cellulose butyrate, natural resins or synthetic resins (polymerization or condensation resins) such as aminoplasts, in particular urea/formaldehyde and melamine/formaldehyde resins, alkyd resins, phenolic plastics, polycarbonates, polyolefins, polystyrene, polyvinyl chloride, polyamides, polyurethanes, polyester, ABS, ASA, polyphenylene oxides, vulcanized rubber, casein, silicone and silicone resins as well as their possible mixtures with one another.

It is also possible to use high molecular weight organic materials in dissolved form as film formers, for example boiled linseed oil, nitrocellulose, alkyd resins, phenolic resins, melamine/formaldehyde and urea/formaldehyde resins as well as acrylic resins.

Said high molecular weight organic compounds may be obtained singly or in admixture, for example in the form of granules, plastic materials, melts or in the form of solutions, in particular for the preparation of spinning solutions, paint systems, coating materials, inks or printing inks.

In a particularly preferred embodiment of this invention, the novel DPP polymers are used for the mass coloration of polyvinyl chloride, polyamides and, especially, polyolefins such as polyethylene and polypropylene as well as for the preparation of paint systems, including powder coatings, inks, printing inks and coating colours.

Illustrative examples of preferred binders for paint systems are alkyd/melamine resin paints, acryl/melamine resin paints, cellulose acetate/cellulose butyrate paints and two-pack system lacquers based on acrylic resins which are crosslinkable with polyisocyanate. According to observations made to date, the novel DPP polymers can be added in any desired amount to the material to be coloured, depending on the end use requirements. In the case of high molecular weight organic materials, for example, the pigments composed according to this invention can be used in an amount in the range from 0.01 to 40, preferably from 0.1 to 20% by weight, based on the total weight of the coloured high molecular weight organic material.

The pigmenting of the high molecular weight organic materials with the novel DPP polymers is usually effected by incorporating said novel DPP polymers, if desired in the form of masterbatches, in the high molecular weight organic materials using customary apparatus suitable to this end, such as extruders, roll mills, mixing or milling apparatus. The material thus treated is then normally brought into the desired final form by methods which are known per se, such as calendering, moulding, extrusion moulding, coating, casting, extruding, or by injection moulding.

In a preferred embodiment of this invention, the novel DPP monomers can be polyreacted in an extruder together with other monomers, in particular with those monomers which are customarily used for the preparation of the aforementioned polymers (reactive extrusion, for example in general accordance with the process disclosed in EP-A 337 951). Copolymers prepared in this manner usually have the same spectrum of application as the blends so far cited consisting of novel DPP polymers and high molecular weight organic materials.

To produce non-brittle mouldings or to diminish their brittleness, so-called plasticizers can be added to the high molecular weight substances prior to moulding. Plasticizers may be, for example, esters of phosphoric acid, phthalic acid and sebacic acid. Said plasticizers may be added before, during or after pigmenting the high molecular weight substances with the DPP polymers of this invention.

To obtain different shades, the novel DPP polymer s may advantageously be used in admixture with fillers, transparent and opaque white, coloured and/or black pigments as well as customary luster pigments in the desired amount.

For the preparation of paints systems, coating materials, inks and printing inks, the corresponding high molecular weight organic substances, such as binders, synthetic resin dispersions etc. and the novel DPP polymers are usually dispersed or dissolved together, if desired together with customary additives such as fillers, paint auxiliaries, siccatives, plasticizers and/or additional pigments, in a common solvent or mixture of solvents. This can be achieved by dispersing or dissolving the individual components by themselves, or also several components together, and only then bringing all components together, or by adding everything together at once.

For application in printing, all customary industrial printing processes can be employed, such as screen printing, rotogravure, bronze printing, flexographic printing and offset printing.

The Examples which follow illustrate the invention.

Preparation of DPP monomers

Example 1a: 16.6 g of sodium and 0.24 g of sodium di-2-acetylhexyl sulfosuccinate are added, with gassing by nitrogen, to 290 ml of tert-amyl alcohol. The mixture is heated at 95°–102° C. with gentle stirring. As soon as the sodium has melted, the emulsion is stirred vigorously at 95°–102° C. for 3 to 5 hours. The solution thus obtained is admixed firstly with 64.0 g (0.48 mol) of p-methoxybenzonitrile. Using a metering pump, 484.8 g (2.4 mol) of diisopropyl succinate dissolved in 24 ml of tert-amyl alcohol are added over the course of 3 hours at 105°–110° C. The isopropanol which forms is distilled off continuously. After the end of the metered addition, the mixture is held at 105°–110° C. for 2 hours more, cooled to 65° C., diluted with methanol, slowly neutralized with glacial acetic acid and heated briefly to reflux temperature. The pigment suspension obtained is filtered at about 50° C. Finally, the residue is washed with methanol and water until colourless and is dried in vacuo at 80° C., to give a good yield of the desired product of the formula

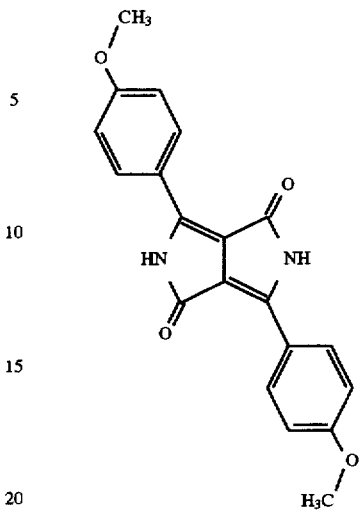

The NMR spectrum in CDCl$_3$/p.a. is in complete agreement with the target structure.

Example 1b: 20.21 g (0.060 mol) of the product from Example 1 a are weighed out directly into a sulfonating flask which is thoroughly flushed with nitrogen; then, 270 ml of dimethyl-formamide are added and the mixture is heated to 130°–135° C. with stirring and with nitrogen being supplied. After 30 minutes, 12.44 g (0.090 mol) of potassium carbonate (dried at 250° C.) are added. 15.18 g (0.090 mol) of 1-(2-bromoethoxy)-2-ethoxyethane dissolved in 30 ml of dimethylformamide are added dropwise over the course of 15 minutes to the dark violet suspension. The resulting dark brown suspension is stirred at 130°–135° C. for 4 ½ hours, then cooled to room temperature and stirred overnight. It is subsequently filtered, and the filter residue is washed with dimethylformamide. The filtrate is concentrated to about 150 ml on a rotary evaporator. The product crystallizes out and is recrystallized from 200 ml of ethanol and dried in a vacuum oven at 40°–50° C., to give 8.42 g (30% of theory) of the product of the formula

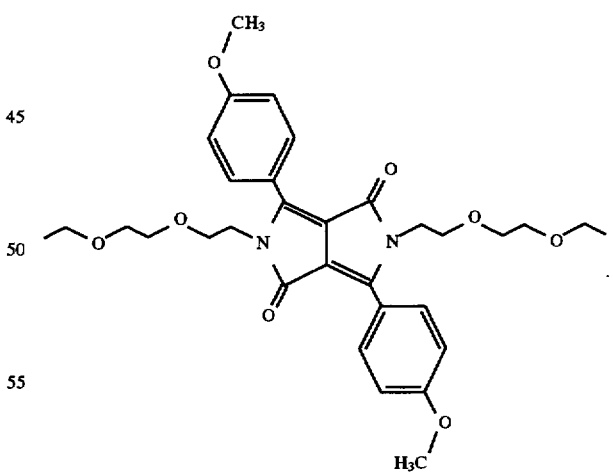

The NMR spectrum in CDCl$_3$/p.a. is in complete agreement with the target structure.

Example 1c: Boron tribromide (36 ml, 0.060 mol) in CH$_2$Cl$_2$ (50 ml) is added slowly at −78° C. to a solution of the product from Example 1b (5 g, 0.010 mol) in CH$_2$Cl$_2$ (50 ml). The solution is warmed slowly to room temperature and stirred for 24 hours. Water (50 ml) is slowly added to the solution. The resulting mixture is subjected to extraction with dichloromethane (3×60 ml). The combined organic phases are dried over magnesium sulfate and concentrated. The crude product is recrystallized from dimethyl sulfoxide, to give 3.9 g of the product of the formula

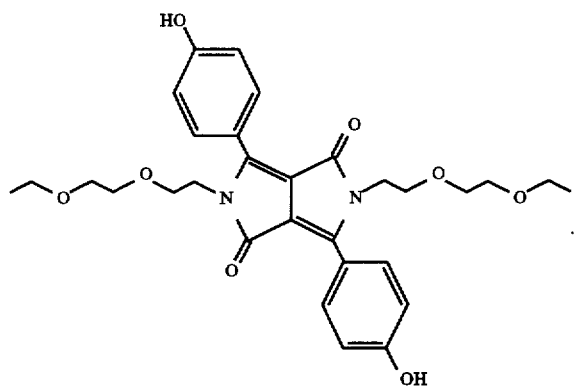

The NMR spectrum in CDCl₃/p.a. is in complete agreement with the target structure.

Example 2: 19.55 g (0.04 mol) of the product from Example 1 c, 0.04 g (2×10⁻⁴ mol) of phenothiazine as catalyst, and 380 ml of dichloroethane are placed under nitrogen in a sulfonating flask and are heated to reflux. 14.48 g (0.16 mol) of acryloyl chloride are added dropwise with stirring to the cloudy solution over the course of about 30 minutes, under reflux (80° C.). After the end of the addition, washing is carried out with 20 ml of dichloroethane. The solution is stirred at reflux for 7 hours, then cooled to room temperature and left to stand overnight. The orange-red, very slightly cloudy solution is washed in a separating funnel 5 times with 100 ml of 5% sodium hydroxide solution and 2 times with deionized water, and is dried over MgSO₄·H₂O and filtered. The filtrate is concentrated to dryness in a rotary evaporator. The red oil which remains solidifies overnight to form a solid mass which is recrystallized from ethanol to give 23.1 g (96.7% of theory) of a crystalline product of the formula

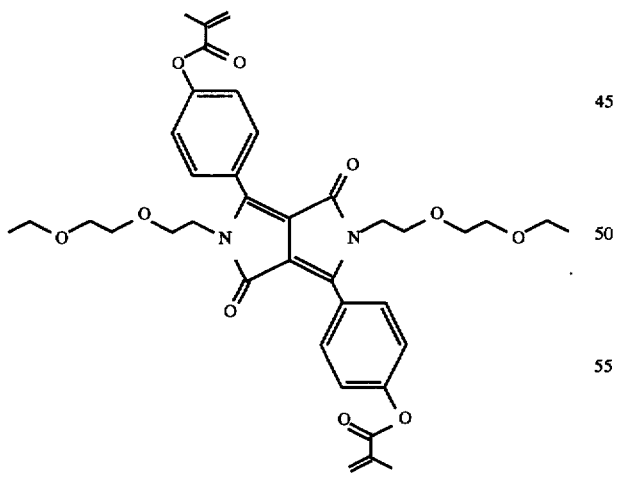

The NMR spectrum in CDCl₃/p.a. is in complete agreement with the target structure.

Example 3a: 53 g (0.40 mol) of 4-cyanobenzaldehyde, 34.5 ml (0.48 mol) of 1,3-propanediol, 9.19 g (0.048 ml) of tosylic acid and 1 l of benzene are placed in a sulfonating flask fitted with stirrer and Dean-Stark separator with condenser. The mixture is stirred at reflux for 5 hours. During this time, about 7 ml of water are deposited in the separator. The resulting reaction mixture is cooled to room temperature and subjected to extraction, firstly with 2% sodium bicarbonate solution (2×500 ml) and then with distilled water (2×500 ml). The organic phase is dried over MgSO₄. The solvent is removed in vacuo and the solid product is dried at 60° C. in vacuo to give 68.2 g (90.1% of theory) of a white compound of the formula

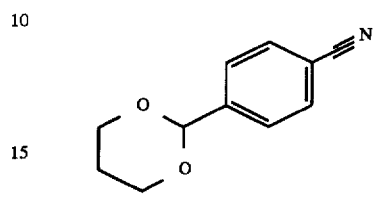

with a melting point of 108°–109° C.

| Analysis: | C | H | N |
|---|---|---|---|
| calculated: | 69.83% | 5.86% | 7.40% |
| found: | 69.88% | 5.87% | 7.10% |

Example 3b: A mixture of 6.90 g (0.3 mol) of sodium and 600 ml of tert-amyl alcohol is stirred under nitrogen and heated to 100° C. At this temperature, the sodium has melted. After further stirring for 16 hours, a clear solution is obtained. 37.8 g (0.2 mol) of the product from Example 3a are added, followed by 20.2 g (0.1 mol) of diisopropyl succinate. The reaction goes on for 28 hours more at the same temperature. The reaction mixture is subsequently cooled to room temperature and poured into a mixture consisting of 45 ml of acetic acid and 1400 ml of methanol. The product (fine crystals) is isolated by filtration, washed first with methanol and then with water, and dried at 80° C. in vacuo, to give 18.0 g (39% of theory) of a dark red product of the formula

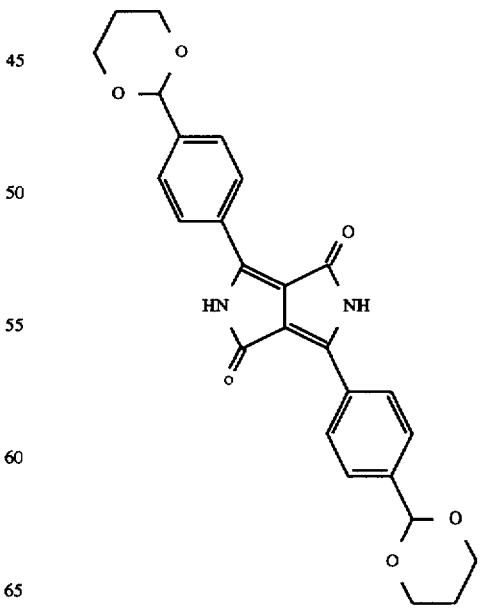

| Analysis: | C | H | N |
|---|---|---|---|
| calculated: | 67.82% | 5.25% | 6.08% |
| found: | 67.71% | 5.29% | 6.07% |

Example 3c: A suspension consisting of 6.70 g (0.0145 mol) of the product from Example 3b, 300 ml (0.6 mol) of aqueous 2M hydrochloric acid and 350 ml of tetrahydrofuran is stirred at reflux for 70 hours and then cooled to room temperature. The dark red product is isolated by filtration, washed with methanol and water and dried at 60° C. in vacuo to give 4.86 g (97% of theory) of a product of the formula

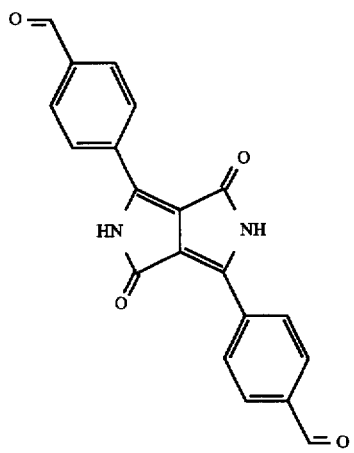

| Analysis: | C | H | N |
|---|---|---|---|
| calculated: | 69.76% | 3.51% | 8.14% |
| found: | 68.58% | 3.66% | 8.09% |

Example 4: A reaction mixture consisting of 4.14 g (0.012 mol) of the product from Example 3c, 0.85 g (0.0068 mol) of 4-dimethylaminopyridine and 13.8 g (0.063 mol) of di-tert-butyl dicarbonate in 250 ml of tetrahydrofuran is stirred at room temperature for 24 hours. A further 5.2 g (0.024 mol) of di-tert-butyl dicarbonate are added, and the reaction mixture is stirred for 5 hours more. The solvent is evaporated under reduced pressure. The moist residue is mixed with 25 ml of methanol, stirred for 30 minutes, filtered, washed with more methanol and finally dried at room temperature in vacuo, to give a good yield of an orange-coloured crystalline product of the formula

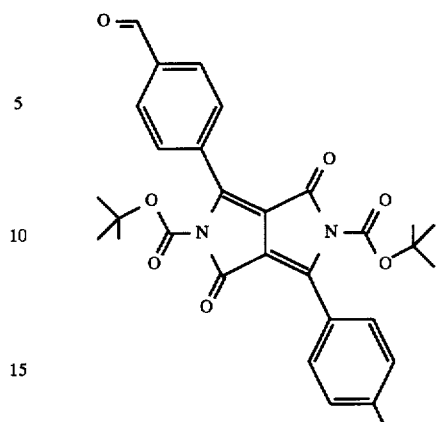

Preparation of DPP polymers

Example 5: 5.13 g (0.01 mol) of the product from Example 1c and 60 ml of chlorobenzene are placed under nitrogen in a sulfonating flask and are heated at gentle reflux. At 129° C. a further 30 ml of chlorobenzene are added. 1.68 g (0.01 mol) of hexamethylene diisocyanate are added dropwise over the course of 15 minutes to the slightly cloudy solution at 130° C. 40 minutes after the end of the addition (and at unchanged temperature) a virtually clear solution is present. After a reaction period of 75 minutes, 0.013 g of dimethylcyclohexylamine (1.0 mol-% solution in chlorobenzene) as catalyst is added. After a further 3 ¼ hours, the solution has become a fine suspension. This suspension is stirred at the same temperature overnight and then cooled to room temperature. The orange-red suspension is filtered and the product is dried at 60°–70° C. in vacuo to give 6.3 g (92.5% of theory) of the desired polyurethane.

In the IR (KBr disc) it is possible to see clearly the characteristic urethane band at 2330 $cm^{-1}$.

Example 6: Photocuring of the DPP bisacrylate monomer 0.80 g of the product from Example 2 is mixed at about 60° C. with 7.2 g of the one-component acrylic resin Cibatool®SL 5154* (a blend comprising acrylate monomers, CIBA-GEIGY AG), and the resulting orange-red solution is briefly degassed in vacuo.

*(already contain photoinitiator and sensitizer)

B) Application

An Erichsen triangular film-drawing instrument is used to prepare films about 100 μm thick on glass, which are subsequently exposed with the aid of a Hoenle UV lamp from a distance of 20 cm and with the 60% setting.

After an exposure time of 30 minutes, the DPP bisacrylate in this formulation is completely insoluble in dimethylformamide, which indicates complete crosslinking.

What is claimed is:
1. A 1,4-diketopyrrolopyrrole of the formula

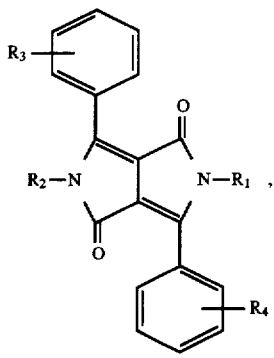

(I)

in which $R_1$ and $R_2$ independently of one another are hydrogen, $C_{12}$-$C_{24}$alkyl, $C_6$-$C_{24}$alkyl which is interrupted one or more times by O or S, or are a group of the formula

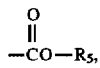

in which $R_5$ is $C_4$-$C_{18}$alkyl or $C_5$-$C_{10}$cycloalkyl, $R_3$ is a polymerizable reactive group, $R_4$, if $R_1$ and $R_2$ are hydrogen, is $C_6$-$C_{24}$alkyl which is attached directly or by way of O or S to the benzene ring and is uninterrupted or is interrupted one or more times by O or S, and $R_4$, if $R_1$ and/or $R_2$ are $C_{12}$-$C_{24}$alkyl, is $C_6$-$C_{24}$alkyl which is interrupted one or more times by O or S or is a group

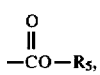

hydrogen, halogen, methyl, methoxy, CN or phenyl, or is the same as $R_3$.

2. A diketopyrrolopyrrole according to claim 1, of the forumula I, wherein $R_3$ is OH, SH, $NH_2$, CHO, NCO, hydroxyphenyl, —CH═$CH_2$, —CH═CH—$COOR_6$, —CH═CH—CN, —O—C(O)—CH═$CH_2$, —O—C(O)—C(Me)═$CH_2$,

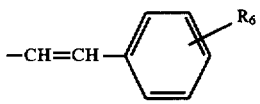

or $COOR_6$, in which $R_6$ is hydrogen or $C_1$-$C_6$alkyl, or $R_3$ is a group of the formula —A—$(CH_2)_m$—CH═CH—$(CH_2)_n$—$CH_3$  (II)

or

—A—$(Y)_p$—X—$(Z)_r$—Q  (III)

in which A is —O—, —NH— or —COO—, m and n independently of one another are an integer between zero and 12, and p and r, independently of one another, are zero or 1, X is methylene or $C_2$-$C_{18}$alkylene which is uninterrupted or is interrupted one or more times by —O— and/or —S—, —NH—, phenylene, —COO—, —CONH—, or

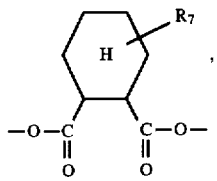

in which $R_7$ is hydrogen or methyl,

Y is

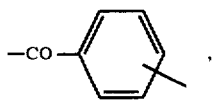

—Si(Cl)$_2$—, —Si($OC_2H_5$)$_2$—, —Si($OCOCH_3$)$_2$—, —$CH_2$—CH(OH)— or —CH(CN)— and Z is —O—, —NH—, —COO—, phenylene,

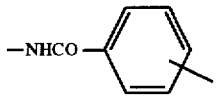

—Si(Cl)$_2$—, —Si($OC_2H_5$)$_2$— or —Si($OCOCH_3$)$_2$—,

Q is —OH, —$NH_2$, glycidyl, —CHO, —NCO, —CH═$CH_2$, —C($CH_3$)═$CH_2$, —CO—CH═$CH_2$, —CO—C($CH_3$)═$CH_2$, $C_5$-$C_7$cycloalkenyl,

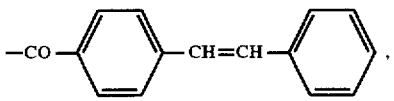

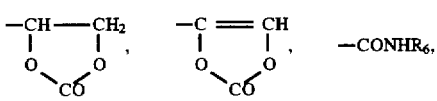, —CONHR$_6$,

—COOR$_6$, —COR$_6$,

where s is an integer from 1 to 6.

3. A diketopyrrolopyrrole according to claim 1, of the forumula I, wherein $R_1$ and R2 are hydrogen and $R_4$ is $C_6$-$C_{18}$alkyl attached directly or by way of O to the benzene ring, or is a group—O($CH_2CH_2O$)$_x$$CH_2CH_3$, in which x is 1, 2, or 3.

4. A diketopyrrolopyrrole according to claim 2, of the forumula I, wherein at least one of the group $R_1$ and $R_2$ is $C_{12}$-$C_{18}$alkyl, a group ($CH_2CH_2O$)$_x$$CH_2CH_3$, in which x is 1, 2 or 3, or a group of the formula

$R_3$ is as defined in claim 2, and $R_4$ is hydrogen or is as defined for $R_3$.

5. A diketopyrrolopyrrole according to claim 2, of the forumula I, wherein $R_3$ is OH, $NH_2$ or a group of the formula $$-X-(O)_r-Q \quad (IV)$$

in which

X is $C_4$–$C_{12}$alkylene which is uninterrupted or is interrupted 1, 2 or 3 times by O and/or once by —S—, —NH— or

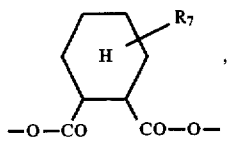

r and $R_7$ are as defined above, and

Q is —OH; —CH=$CH_2$, —C($CH_3$)=$CH_2$, —CO—CH=$CH_2$ or —CO—C($CH_3$)=$CH_2$.

6. A diketopyrrolopyrrole of the formula

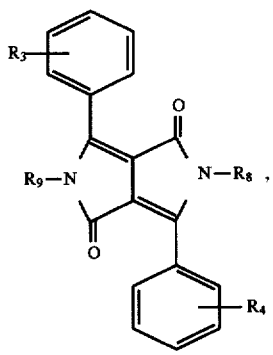

(XIII)

in which $R_8$ is a group $$-(CH_2)_m-CH=CH-(CH_2)_n-CH_3 \text{ or}$$

$$-(Y)_p-X-(Z)_r-Q$$

and $R_9$ is hydrogen or is $R_8$, $R_3$ is a polymerizable reactive group, $R_4$, if $R_1$ and $R_2$ are hydrogen, is $C_6$–$C_{24}$alkyl which is attached directly or by way of O or S to the benzene ring and is uninterrupted or is interrupted one or more times by O or S, and $R_4$, if $R_1$, and/or $R_2$ are $C_{12}$–$C_{24}$alkyl, is $C_6$–$C_{24}$alkyl which is interrupted one or more times by O or S or is a group,

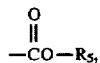

in which $R_5$ is $C_4$–$C_{18}$ alkyl or $C_5$–$C_{10}$cycloalkyl hydrogen, halogen, methyl, methoxy, CN or phenyl, or is the same as $R_3$ and X, Y, Z, Q, m, n, p and r are as defined in claim 2.

7. A process for preparing a diketopyrrolopyrrole according to claim 1 by reacting a succinic diester with a nitrile, which comprises (a) reacting an asymmetric or symmetric dialkyl or diaryl succinate, or a monoalkyl monoaryl succinate or dicyclohexyl succinate, with a nitrile of the formula

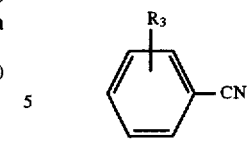

or with a mixture of the nitriles of the formulae

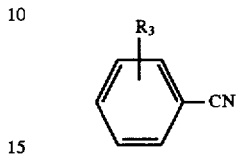

and

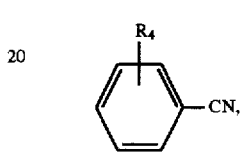

where $R_3$ and $R_4$ are as defined in claim 1 and may additionally be customary protective groups, in the desired molar ratio in an organic solvent in the presence of a strong base, and then hydrolysing the reaction product and, optionally, isolating the desired product, and (b) optionally reacting the resulting diketopyrrolopyrroles of the formula I in which $R_1$ and $R_2$ are hydrogen with (b1) a dicarbonate of the formula XI,

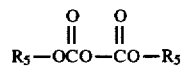

in the desired molar ratio, or (b2) reacting it in the desired molar ratio with a halogen compound of the formula XII, $R_1$—Hal, in which $R_1$ is $C_{12}$–$C_{24}$alkyl or is $C_6$–$C_{24}$alkyl which is interrupted one or more times by O or S, or (b3) reacting it in the desired molar ratio with a halogen compound of the formula $$Hal-(CH_2)_m-CH=CH-(CH_2)_n-CH_3 \text{ or } Hal-(Y)_p-X-(Z)_r-Q$$

in which m and n independently of one another are an integer between zero and 12, and p and r, independently of one another, are zero or 1, X is methylene or $C_2$–$C_{18}$alkylene which is uninterrupted or is interrupted one or more times by —O— and/or —S—, —NH—, phenylene, —COO—, —CONH—, or

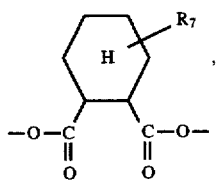

in which $R_7$ is hydrogen or methyl,

Y is

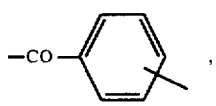

—Si(Cl)$_2$—, —Si(OC$_2$H$_5$)$_2$—, —Si(OCOCH$_3$)$_2$—, —CH$_2$—CH(OH)— or —CH(CN)— and Z is —O—, —NH—, —COO—, phenylene,

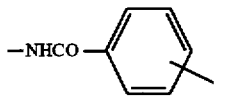

—Si(Cl)$_2$—, —Si(OC$_2$H$_5$)$_2$— or —Si(OCOCH$_3$)$_2$—,

Q is —OH, —NH$_2$, glycidyl, —CHO, —NCO, —CH=CH$_2$, —C(CH$_3$)=CH$_2$, —CO—CH=CH$_2$, —CO—C(CH$_3$)=CH$_2$, C$_5$–c$_7$cycloalkenyl,

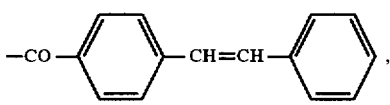

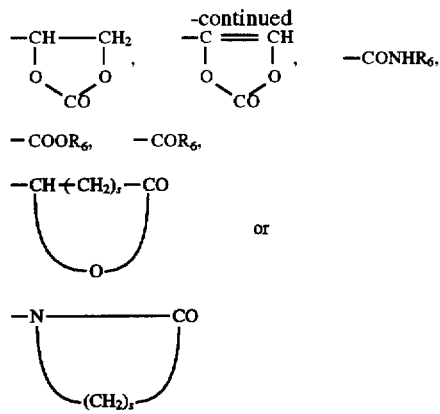

in which R$_6$ is hydrogen or C$_1$–C$_6$alkyl and s is an integer from 1 to 6, and (c) optionally, reacting a diketopyrrolo-pyrrole of the formula I in which R$_3$ and/or R$_4$ are protective groups in a customary manner, directly prior to or following step b, to give the corresponding diketopyrrolopyrrole according to claim 1.

* * * * *